United States Patent [19]

Hoshino

[11] Patent Number: 4,985,029
[45] Date of Patent: Jan. 15, 1991

[54] LASER APPARATUS FOR MEDICAL TREATMENT

[76] Inventor: Masahiko Hoshino, 989-3, Ohaza Uchino Hongo, Ohmiya-Shi, Saitama, Japan

[21] Appl. No.: 360,609

[22] Filed: Jun. 2, 1989

[30] Foreign Application Priority Data

Jan. 11, 1989 [JP] Japan .................................. 1-4510

[51] Int. Cl.⁵ .............................................. A61B 17/36
[52] U.S. Cl. ..................................... 606/16; 606/13; 350/96.1
[58] Field of Search ......................... 606/2, 13–16; 128/303.1, 4–7; 350/96.1, 96.3, 96.24

[56] References Cited

U.S. PATENT DOCUMENTS

| 4,273,109 | 6/1981 | Enderby | 606/16 X |
|---|---|---|---|
| 4,313,431 | 2/1981 | Frank | 606/16 X |
| 4,526,170 | 7/1985 | Tanner | 606/16 X |
| 4,740,047 | 4/1988 | Abe et al. | 350/96.1 X |
| 4,743,084 | 5/1988 | Manning | 350/96.1 X |
| 4,746,194 | 5/1988 | Rasmussen | 350/96.1 X |
| 4,762,385 | 8/1988 | Fuse | 350/96.1 X |
| 4,819,630 | 4/1989 | DeHart | 606/16 X |
| 4,842,390 | 6/1989 | Sottini et al. | 128/5 X |
| 4,850,351 | 7/1989 | Herman et al. | 606/7 |

Primary Examiner—Robert A. Hafer
Assistant Examiner—Kerry Owens
Attorney, Agent, or Firm—Nilles & Nilles

[57] ABSTRACT

A laser treatment apparatus wherein a tip member formed of a light-transmitting material having a low thermal conductivity and a high heat-resistant property is integrally welded to the tip portion of a fiber waveguide member connected to a laser beam source. A connecting portion having substantially the same diameter as that of a core portion of the fiber waveguide member is integrally formed on the tip member so that end surfaces of the connecting portion and of the core portion are integrally welded to each other. A cladding part leading to a clad formed on the circumference of the core portion is formed on the outer peripheries of the connecting portion and of a welded portion between an end surface of the connecting portion and an end surface of the core portion. External portions of the fiber waveguide member and of the tip member are connected to each other through a sleeve.

3 Claims, 4 Drawing Sheets

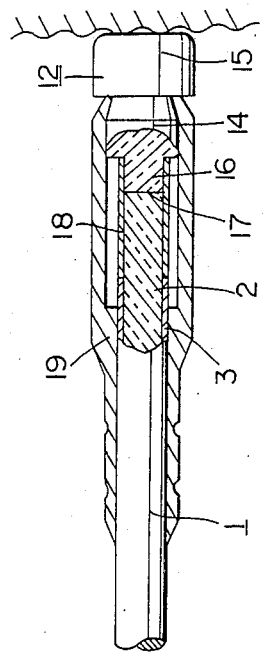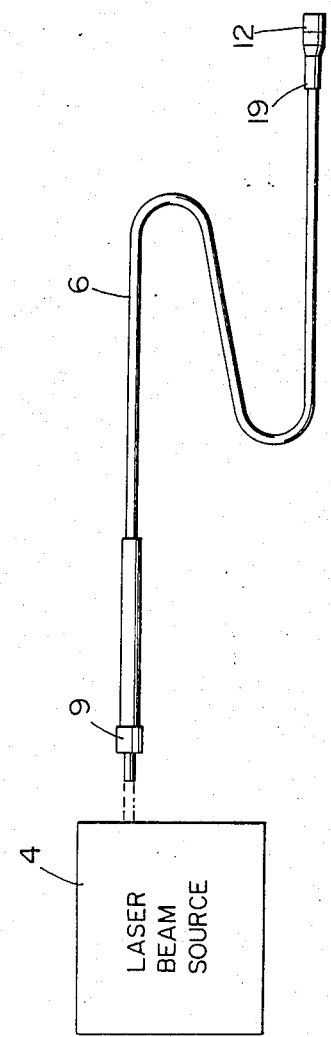

LASER APPARATUS FOR MEDICAL TREATMENT

BACKGROUND OF THE INVENTION:

1. Field of the Invention:

The present invention is directed to a laser treatment apparatus for guiding a laser beam through an optical fiber for the incision, vaporization or coagulation of a target tissue, or for photochemical therapy.

2. Description of the Prior Art:

A well-known laser apparatus for medical treatment has a typical construction depicted in, e.g., FIGS. 8 and 9.

A fiber waveguide member generally designated at 1 includes a core portion 2 and a clad 3. Core portion 2 assumes a substantially circular configuration in cross section and is formed of a light-transmitting material having a low thermal conductivity and a high heat-resistant property such as silica glass or potash glass. Clad 3 is formed on the outer periphery of core portion 2. An output end of core portion 2 is so cut off as to have a surface perpendicular to the optical axis, and is then ground. An input end on the opposite side of core portion 2 is connected to a laser beam source 4. Coaxially provided on the outer periphery of fiber waveguide member 1 is an external tube 6 having a spatial portion 5 serving as, for instance, a water or air passageway. Fixed to the tip of external tube 6 is a holding member 8 formed with an insertion hole 7 into which fiber waveguide member 1 is inserted. An optical connector 9, which is connected to laser beam source 4, is provided at the input end of external tube 6. There is further formed a branch tube 10, the interior of which communicates with spatial portion 5 for sending a liquid or gas to external tube 6. The liquid or gas is fed in from the end of branch tube 10.

The laser beams from laser beam source 4 are led via fiber waveguide member 1 and are then emitted from the output end of the tip of fiber waveguide member 1. At this time, living tissues organized at spacings of several millimeters are irradiated with the laser beams at divergent angles of approximately 8°-12° from the output end of fiber waveguide member 1. On the occasion of irradiation, the irradiation surfaces may be damaged by contaminant such as tissues, tissue liquid and smoke emitted by their vital reaction. With a view to preventing this damage, an assist gas or water is sent from branch tube 10 via spatial portion 5 to the tip output end of fiber waveguide member 1, thereby eliminating the contamination on the output end.

In fact, however, the contamination on the tip end portion can not sufficiently be prevented, depending on the assist gas or water, and the tip end portion is burnt, thereby causing a damage. In order to adjust the divergent angles of laser beams to the purposes of medical treatment, in some cases the tip output end of fiber waveguide member 1 is shaped in a conical or semispherical configuration, but it can easily be damaged by the contamination or diffused rays of light.

FIG. 10 illustrates a known fiber treatment apparatus which effects the medical treatment by directly touching the living. This type of apparatus is arranged such that the tip of holding member 8 of the laser treatment apparatus depicted in FIG. 8 is fitted with a connector 11 connected to a tip member 12 formed of a light-transmitting material like, e.g., artificial sapphire ($\alpha$-Al$_2$O$_3$), tip member 12 being so secured to the axis of fiber waveguide member 1 as to be spaced therefrom. Formed in the cylindrical portion of connector 11 around the spacing between tip member 12 and fiber waveguide member 1 are discharge holes 13 from which the assist gas or water is discharged.

There arises, however, the following problem inherent in the laser treatment apparatus depicted in FIG. 10. The apparatus is in contact with the tissues, and hence a contaminant permeates from discharge hole 13 and contaminates the optical axis of tip member 12 as well as fiber waveguide member 1. This results in damage to fiber waveguide member 1 and tip member 12 due to the burnt loss associated with the contaminant by the laser beams.

As described above, the laser treatment apparatus illustrated in FIG. 8 is attended with the problem that the tip end surface of fiber waveguide member 1 undergoes burning due to contamination, resulting in the damage to fiber waveguide member 1.

The laser treatment apparatus also has the problem in which the optical axis positioned in the spacing between fiber waveguide member 1 and tip member 12 is contaminated and undergoes the burning, with the result that the fiber waveguide member 1 and tip member 12 are damaged.

In either case, the contamination has to be eliminated and it is further required that fiber waveguide member 1 be cooled down by using the assist gas or water. Hence, these laser treatment apparatuses are not allowed for use in such places that the assist gas or water can not be employed.

SUMMARY OF THE INVENTION

It is therefore a primary object of the present invention to provide a novel laser treatment apparatus which is hard to be damaged.

According to one aspect of the invention, there is provided a laser treatment apparatus characterized in that a tip member formed of a light-transmitting material having a low thermal conductivity and a high heat-resistant property is integrally welded to the tip portion of a fiber waveguide member connected to a laser beam source.

According to another aspect of the invention, there is provided a laser treatment apparatus characterized in that a connecting portion having substantially the same diameter as that of a core portion of a fiber waveguide member is integrally formed on a tip member, and end surfaces of the connecting portion and of the core portion are integrally welded to each other.

According to still another aspect of the invention, there is provided a laser treatment apparatus characterized in that a fiber waveguide member includes a core portion and a clad formed on the circumference of the core portion, and a cladding part leading to the clad is formed on the outer peripheries of a connecting portion of a tip member and of a welded portion between an end surface of the connecting portion and an end surface of the core portion.

According to a further aspect of the invention, there is provided a laser treatment apparatus characterized in that external portions of a fiber waveguide member and of a tip member are connected to each other through a sleeve.

According to a still further aspect of the invention, there is provided a laser treatment apparatus characterized in that a fiber waveguide member and a tip member are formed into one united body by welding, and laser beams emerging from a laser beam source are emitted out of the tip member via the fiber waveguide member.

According to yet another aspect of the invention, there is provided a laser treatment apparatus characterized in that a welding process is facilitated by integrally welding an end surface of the fiber waveguide member to an end surface of a connecting portion formed on a tip member.

According to a yet further aspect of the invention, there is provided a laser treatment apparatus characterized in that a cladding part leading to a clad is formed on the outer peripheries of a connecting portion of a tip member and of a welded portion between an end surface of the connecting portion and an end surface of a core portion of a fiber waveguide member, thereby minimizing damages caused by a leakage of light and contamination.

According to a still additional aspect of the invention, there is provided a laser treatment apparatus characterized in that the external portions of a tip member and of a fiber waveguide member are connected to each other and reinforced by use of a sleeve.

BRIEF DESCRIPTION OF THE DRAWINGS:

Other objects and advantages of the invention will become apparent during the following discussion in conjunction with the accompanying drawings, in which:

FIG. 1 is a side view with parts partially broken away, illustrating one embodiment of a laser treatment apparatus according to the present invention;

FIG. 2 is a side view showing a state where the laser treatment apparatus is used;

Figure 8:
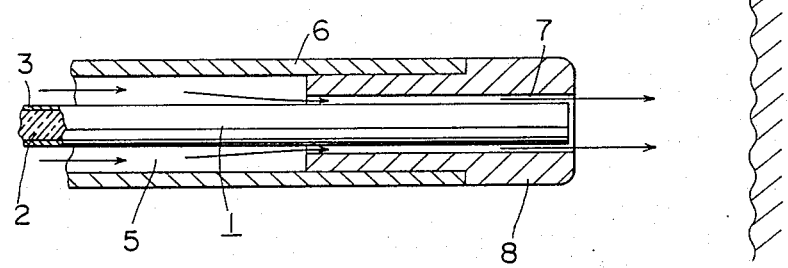
FIG. 8 is a sectional view depicting a conventional laser treatment apparatus.
Figure 9:
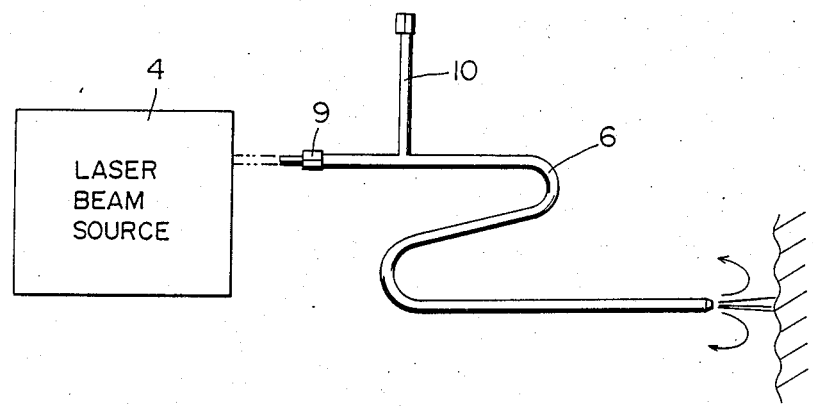
FIG. 9 is a side view showing a state where the prior art apparatus is used.
Figure 10:
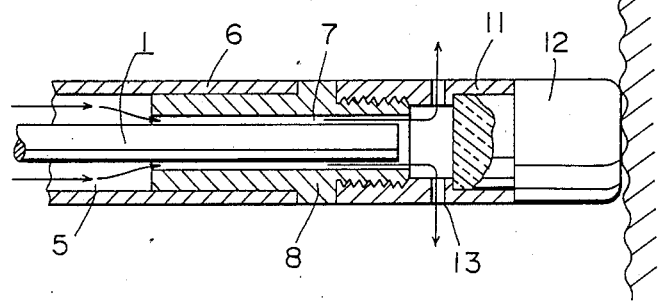
FIG. 10 is a sectional view showing another example of the prior art apparatus.

DESCRIPTION OF THE PREFERRED EMBODIMENTS:

In FIGS. 1 and 2, the same components as those depicted in FIGS. 8 to 10 are marked with the like symbols.

A fiber waveguide member generally indicated at 1 includes a core portion 2 which assumes a substantially circular configuration in cross section and has a diameter of 100-600 μm. Core portion 2 is formed of a light-transmitting material having a low thermal conductivity and a high heat-resistant property such as silica glass ($SiO_2$) or potash glass. Fiber waveguide member 1 also includes a clad 3 formed of an organic material such as silicone having a different refractive index from that of core portion 2. The outer periphery of core portion 2 is covered with clad 3 which is approximately 3-4 m in length.

A tip member 12 is formed of the same material as that of core portion 2 of fiber waveguide member 1. An output end of a body 14 is formed integrally with a laser beam irradiation part 15 assuming a substantially cylindrical shape. An incident end of body 14 is also formed integrally with a cylindrical connecting portion 16 having almost the same diameter as that of core portion 2.

Clad 3 provided at the tip portion of fiber waveguide member 1 is stripped by several millimeters to integrally weld the tip end surface of core portion 2 and the incident end surface of connecting portion 16, thus shaping a welded portion 17. A bonding agent conceived as a cladding material is coated on the outer peripheries of welded portion 17, connecting portion 16 and core portion 2 from which clad 3 is partially stripped so that the coating level is nearly flush with the outer surface of clad 3, thus forming a cladding part 18.

Fixed to the outer periphery of fiber waveguide member 1 is the inside of the proximal end of a metallic sleeve 19 formed in substantially cylindrical configuration. The inner periphery of tip portion of sleeve 19 is also fixed to the outer periphery of body 14 of tip member 12, thereby reinforcing the connection between fiber waveguide member 1 and tip member 12.

Connected to the proximal end of fiber waveguide member 1 is an optical connector 9 by which a laser beam source 4 is connected to core portion 2 of fiber waveguide member 1.

The laser beams emitted from laser beam source 4 are led by core portion 2, and the irradiation of laser beams is effected by a laser beams irradiation part 15 of tip member 12. Then, the tissues of a living are subjected to an incision, vaporization and coagulation or a photochemical therapy.

In the illustrative embodiment described above, the light-emitting end surface of core portion 2 of fiber waveguide member 1 is integrally welded to the light-entering end surface of connector 16 of tip member 12. With this arrangement, the light-emitting end surface of core portion 2 and the light-entering end surface of connecting portion 16 are not contaminated with contaminants such as blood or the like. Damage due to burning is thus prevented.

In applying the cladding material, it will not flow and deposit on the light-emitting end surface of core portion 2 and on the light-entering end surface of connecting portion 16.

The cladding material is applied on the outer peripheries of connecting portion 16, welded portion 17 and the portion from which clad 3 is stripped, thus forming cladding part 18 sealed by sleeve 19. Based on this arrangement, it is feasible to prevent a leakage of light and permeation of contaminants into gaps such as pinholes of cladding part 18. Therefore, the possibility of causing the damages due to burning associated with the contamination can completely be eliminated.

Hence, when laser beams irradiation part 15 of tip member 12 is brought to the seat of a disease in which the light-emitting end tends to be contaminated in a clinical use, the probability of being damaged is small. Besides, the disease seat in which a flow of assist gas or water is not permissible can be treated.

Figure 3:
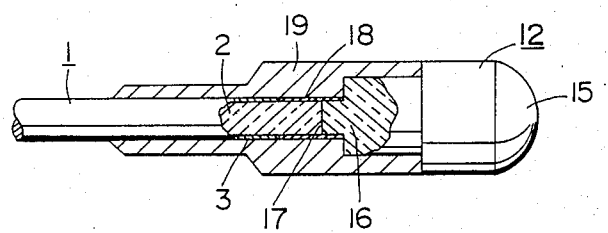
FIGS. 3 to 5 are side views with parts partially broken away, respectively illustrating other embodiments thereof.
Figure 4:
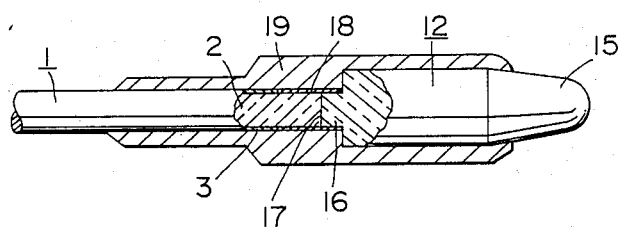
Figure 5:
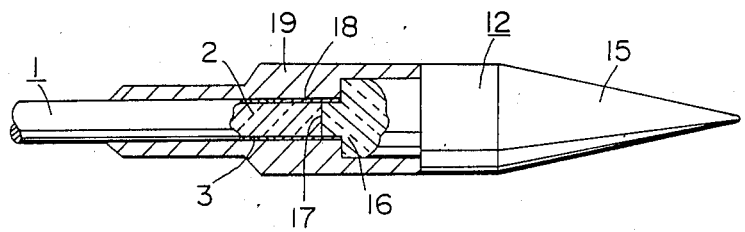

The laser beam irradiation part of tip member 12 may assume arbitrary shapes such as a semispherical configuration illustrated in FIG. 3, or a frust-conical shape in which the tip is, as illustrated in FIG. 4, formed in a spherical configuration, or a conical shape shown in FIG. 5. The angles at which the laser beams are emitted may arbitrarily be set depending on the configuration of tip member 12.

In accordance with the above-described embodiments, laser beam irradiation part 15 can be shaped by rotating tip member 12 without rotating lengthy fiber waveguide member 1.

Furthermore, a member such a spring may be employed instead of metallic sleeve 19.

Figure 6:
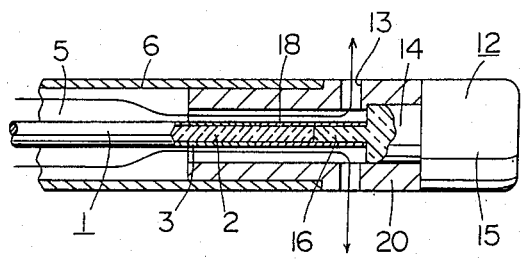
FIG. 6 is a side view with parts partially broken away, showing still another embodiment.
Figure 7:
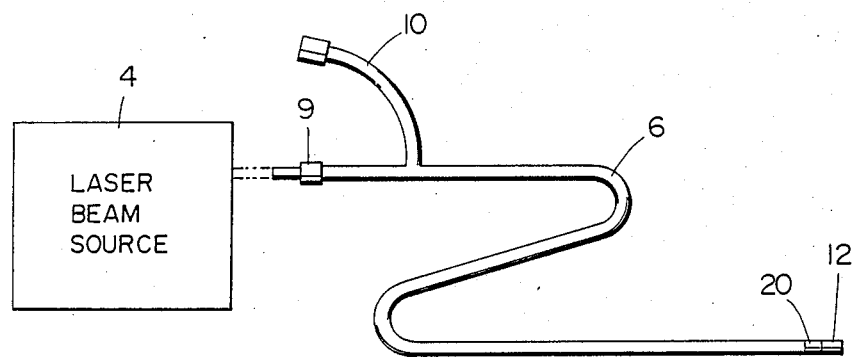
FIG. 7 is a side view illustrating a state where the laser treatment apparatus of FIG. 6 is used.

The description will next be focused on a further embodiment with reference to FIGS. 6 and 7. Provided through a spatial portion 5 on the outer periphery of fiber waveguide member 1 is an external tube 6 having its top end to which a connecting cylinder 20 is connected. The outer periphery of the body 14 of tip member 12 is fixed to the inner peripheral portion of top of connecting cylinder 20 perforated with a discharge hole 13 through which the cylinder interior communicates with the cylinder exterior. A branch tube 10 extending from external tube 6 admits an inflow of assist gas or water.

In the disease seat which does not permit the use of assist gas or water, as in the embodiment shown in FIGS. 1 and 2, the laser beams emerging from laser beams source 4 are led by core portion 2 of fiber waveguide member 1, and the irradiation thereof is effected by laser beams irradiation part 15 of tip member 12 without using the assist gas or water.

In the disease seat wherein the assist gas or water is allowed to be employed, if the cooling of fiber waveguide member 1 is needed, the assist gas or water is fed in from branch tube 10 and is then transmitted via spatial portion 5. Fiber waveguide member 1 and tip member 12 are thus cooled down.

In accordance with the embodiment of FIGS. 6 and 7, the laser treatment apparatus can be used under such circumstances that there exist contaminations in the tissue liquid or blood, or a sufficient cooling function is not provided in the air.

As discussed above, the present invention exhibits the following effects. The tip member is welded to the top end of the fiber waveguide member, thus forming the fiber waveguide member and the tip member into one united body. This arrangement prevents the contamination on the laser beam axis, thereby causing no burning, which in turn reduces the damages to the tip member.

The connecting portion of the tip member has almost the same diameter as that of the core portion, thereby facilitating the welding process.

In addition, the cladding part leading to the clad is formed on the outer peripheries of the welded portion as well as of the connecting portion. As a result of this arrangement, the leakage of light can be decreased, and the connecting strength increases. Hence, the efficiency of laser beams can be ameliorated. Moreover, a situation is present wherein damages are hard to occur.

The fiber waveguide member is fixedly connected to the tip member by means of the sleeve, and the connection between the fiber waveguide member and the tip member can thereby be reinforced. Consequently, even if the tip member is separated from the fiber waveguide member, the tip member can be held by the sleeve. The treatment can thus be performed under safety conditions.

What is claimed is:

1. A laser treatment apparatus characterized by comprising a fiber waveguide member connected to a laser beam source and having a core presenting a tip portion including a core end surface, and a tip member formed of a light-transmitting material having a low thermal conductivity and a high heat-resistant property, said tip member including an integral connecting portion formed thereon having substantially the same dimension as that of said core portion of said fiber waveguide member and presenting a connecting portion end surface, said end surfaces of said connecting portion and of the core portion integrally welded to each other by a welded portion.

2. The laser treatment apparatus according to claim 1, wherein said connecting portion and welded portion each has an outer periphery, and said core has a circumference with a clad formed on said circumference terminating short of said welded portion to provide an unclad core area and further comprising a cladding part leading from said clad and formed on said unclad core area and on said outer peripheries of said connecting portion and said welded portion.

3. The laser treatment apparatus according to claim 1, wherein said fiber waveguide member and said tip member each have external portions, and further comprising a sleeve connecting said external portions of said fiber waveguide member and of said tip member to each other.

* * * * *